(12) United States Patent
Prance et al.

(10) Patent No.: US 7,924,004 B2
(45) Date of Patent: Apr. 12, 2011

(54) ELECTRIC POTENTIAL SENSOR FOR USE IN THE DETECTION OF NUCLEAR MAGNETIC RESONANCE SIGNALS

(75) Inventors: Robert Prance, Brighton (GB); Terence Clarke, Uckfield (GB)

(73) Assignee: University of Sussex (GB)

( * ) Notice: Subject to any disclaimer, the term of this patent is extended or adjusted under 35 U.S.C. 154(b) by 18 days.

(21) Appl. No.: 12/278,214

(22) PCT Filed: Jan. 24, 2007

(86) PCT No.: PCT/GB2007/000248
§ 371 (c)(1),
(2), (4) Date: Nov. 21, 2008

(87) PCT Pub. No.: WO2007/088328
PCT Pub. Date: Aug. 9, 2007

(65) Prior Publication Data
US 2009/0096447 A1 Apr. 16, 2009

(30) Foreign Application Priority Data
Feb. 3, 2006 (GB) .................................. 0602229.7

(51) Int. Cl.
*G01V 3/11* (2006.01)
(52) U.S. Cl. ........................................ 324/307; 324/309
(58) Field of Classification Search .......... 324/300–322; 600/407–445
See application file for complete search history.

(56) References Cited

U.S. PATENT DOCUMENTS

| 7,109,714 B2 * | 9/2006 | Rudakov et al. ............... 324/322 |
| 7,292,033 B2 * | 11/2007 | Pusiol ............................ 324/307 |
| 7,358,737 B2 * | 4/2008 | Hoult ............................. 324/322 |
| 7,659,124 B2 * | 2/2010 | Pusiol ............................ 436/173 |
| 2008/0147154 A1 * | 6/2008 | Gray et al. ..................... 607/115 |

FOREIGN PATENT DOCUMENTS

| WO | 03/040761 A1 | 5/2003 |
| WO | 03/048789 A2 | 6/2003 |

OTHER PUBLICATIONS

Harland C. J. et. al. "Electric potential probes—new directions in the remote sensing of the human body"; Measurement Science and Technology, vol. 13, Issue 2, pp. 163-169 (Feb. 1, 2002); XP020063427.
Harland C. J. et. al. "Remote detection of human electroencephalograms using ultrahigh input impedance electric potential sensors"; Applied Physics Letters, vol. 81, No. 17, pp. 3284-3286 (Oct. 21, 2002); XP012032293.
Gebrial W. et. al. "Non-invasive imaging using an array of electric potential sensors" Review of Scientific Instruments, vol. 77, 063708 (2006); XP012093113.
International Search Report for International application No. PCT/GB2007/000248 dated May 23, 2007.

* cited by examiner

*Primary Examiner* — Brij B Shrivastav
(74) *Attorney, Agent, or Firm* — Brooks Kushman P.C.

(57) ABSTRACT

The present invention provides nuclear magnetic resonance apparatus comprising means for applying a static magnetic field ($H_0$) to a sample under investigation, a radio frequency circuit arranged to be inductively coupled to the sample by means of an oscillating magnetic field disposed generally perpendicular to the static magnetic field for applying an excitation signal to the sample, and an electric potential sensor ($E_1$, $E_2$) for detecting the excitation of the sample and for generating a detection output. The electric potential sensor comprises an electrode placed generally perpendicular to the axis of the oscillating magnetic field for capacitively coupling the electric potential sensor to the sample.

36 Claims, 9 Drawing Sheets

ELECTRIC POTENTIAL SENSOR FOR USE IN THE DETECTION OF NUCLEAR MAGNETIC RESONANCE SIGNALS

FIELD OF THE INVENTION

The present invention concerns electric potential sensors for use in the detection of signals generated in nuclear magnetic resonance (NMR) apparatus, as well as to a method of NMR signal detection.

The invention may find application in numerous areas, for example in NMR imaging and spectroscopy, and in quantum computers, as well as in medical applications such as Magnetic Resonance Imaging (MRI).

BACKGROUND TO THE INVENTION

Nuclear magnetic resonance (NMR) is a phenomenon which occurs when the nuclei of certain atoms are subjected to a magnetic field in the presence of a second, perpendicular, oscillating magnetic field, and this phenomenon is commonly employed in NMR imaging and spectroscopy to study the physical, chemical or biological properties of samples of matter. This may best be understood by reference to FIG. 1.

Figure 1:
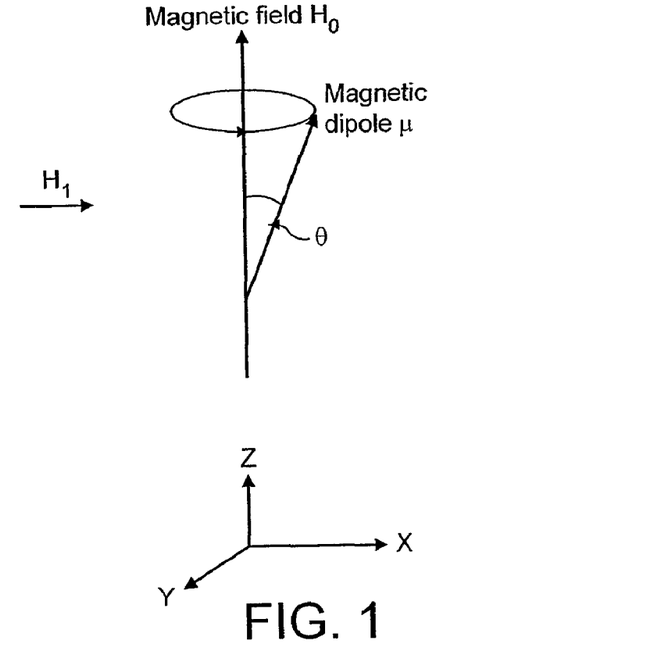
FIG. 1 is a diagram representing the phenomenon of nuclear magnetic resonance (NMR)

Many species of nuclei contain non zero spin and an associated magnetic dipole moment, and it is this which gives rise to nuclear paramagnetism and hence nuclear magnetic resonance (NMR). As shown in FIG. 1, when a static magnetic field $H_0$ is applied to a sample containing nuclear spins, the spins of the various nuclei become aligned in the direction of the Z axis. As a result of the underlying quantum mechanics of the system, the spins will precess around the Z axis at some angle $\theta$, with a rate $\omega_0$ given by the Larmor precession equation:

$$\omega_0 = \gamma H_0$$

where $\gamma$ is the gyromagnetic ratio for the sample under consideration. If an additional radio frequency (RF) field $H_1$ is then applied in a direction perpendicular to the static magnetic field $H_0$ at a frequency $$\omega_{RF} = \omega_0$$

the angle $\theta$ will be increased due to resonant absorption.

Figure 2:
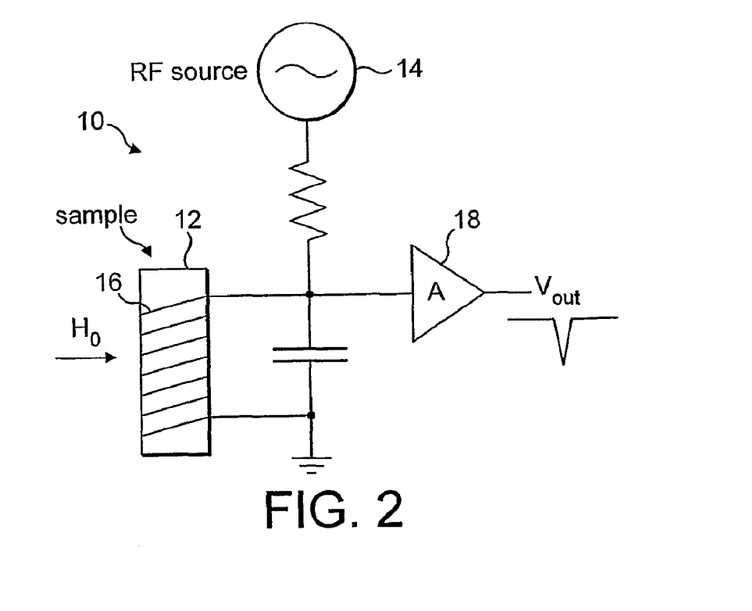
FIG. 2 is a circuit diagram of a conventional NMR apparatus.

There are two conventional forms of NMR apparatus, known respectively as continuous wave NMR apparatus and pulse NMR apparatus, the signal detection in each case being by means of an inductive sensor as shown in FIG. 2. This inductive sensor comprises a resonant circuit 10 used to probe a sample 12 that is situated in a static magnetic field $H_0$. In its simplest implementation, as illustrated, this circuit is used both to supply, and to read the output generated by, an excitation signal applied to the sample 12. For this purpose, RF power is supplied by an RF source 14, which is inductively coupled by means of a coil 16 to the sample 12.

Continuous Wave NMR

In the known continuous wave NMR apparatus, the static magnetic field $H_0$ is swept slowly in amplitude, and when $$\omega_0 = \omega_{RF}$$

absorption occurs and a dip in the signal voltage across the inductive coupling is observed. The same result may also be achieved by fixing the amplitude of the static magnetic field and sweeping the RF frequency. The signal voltage requires a large amount of amplification in order for the dip to be manifest, and is therefore applied to an amplifier 18 for output.

In practice, the slow variation of the static magnetic field $H_0$ is generally achieved by adding a time varying field to the static one. This is often accomplished using additional coils.

Figure 3:
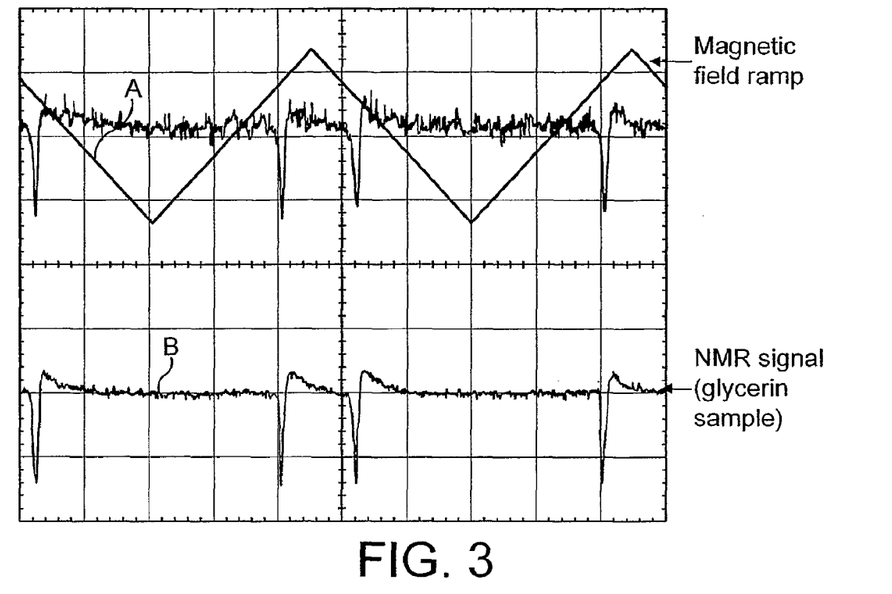
FIG. 3 is a signal diagram illustrating an output signal obtained from the apparatus of FIG. 2 when set up to operate as continuous wave NMR apparatus.

FIG. 3 shows a conventional magnetic continuous wave NMR absorption dip acquired using the apparatus of FIG. 2. The triangular ramp A represents a time varying signal (modulation) added to the static magnetic field $H_0$, and the lower trace B shows the absorption dip for a sample of liquid glycerine. As expected, we see two dips per period of the modulation waveform, one for each time that the static field generates the result $\omega_0 = \omega_{RF}$.

Pulse NMR

Figure 4:
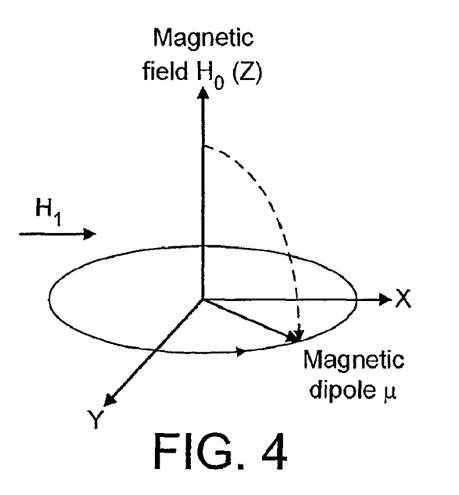
FIG. 4 is a diagram representing the application of a short pulse of RF power in pulse NMR apparatus.

In pulse NMR apparatus, the RF field $H_1$ consists of a short pulse of RF power, the RF pulse being applied to the sample 12 with an amplitude chosen such that the angle $\theta$ of the precessing spins becomes 90°, thereby tipping them from the Z plane into the X-Y plane. This is shown in FIG. 4. Clearly this corresponds to the maximum amplitude of the precession, and a pulse producing this deflection is called a 90° or $\pi/2$ pulse. A 180° or $\pi$ pulse would simply flip the spins to the Z axis antiparallel to the applied static magnetic field. The pulse length is designated as:

$\pi/2$ when $\theta$ is rotated by 90°
$\pi$ when $\theta$ is rotated by 180°

Once the RF pulse has ended, the spins will continue to precess but the amplitude of the precession, the angle $\theta$, will decrease with time due to interaction of the spins of the nuclei with one another. This gives rise to what is known as the free induction decay (FID) signal from the precession of the spins, an exponentially decaying sinewave generally at the Larmor precession frequency. It is the FID signal which is detected in pulse NMR.

In a variation of this arrangement, the applied RF field $H_1$ is selected to have a frequency close to but not quite satisfying the Larmor precession equation $\omega_{RF} = \omega_0$. Mixing then occurs, which gives rise to a lower frequency output signal, which is easier to amplify and filter. This process is known as nutation.

Figure 5:
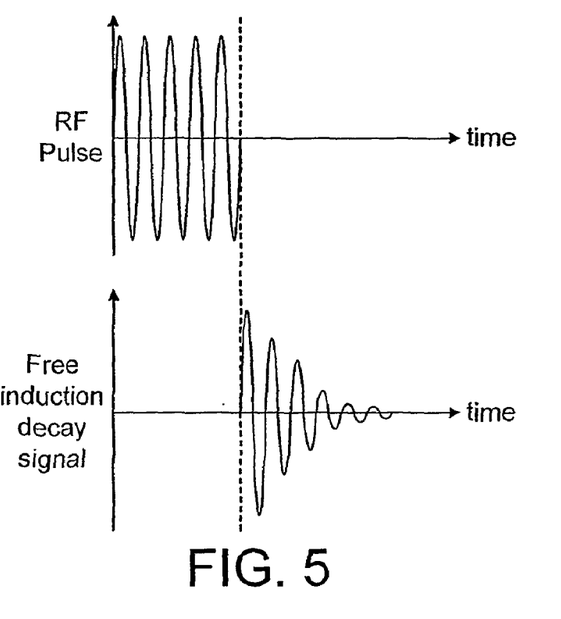
FIG. 5 is a signal diagram representing an output signal obtained from the apparatus of FIG. 2 when set up to operate as pulse NMR apparatus.

Pulse NMR apparatus employs a sensor circuit generally the same as that shown on FIG. 2, with the exception that in this instance the RF source 14 supplies an oscillating pulse of short duration while the static magnetic field $H_0$ is of constant amplitude. FIG. 5 shows a typical NMR $\pi/2$ RF pulse and the resulting FID signal occurring following the pulse.

The known inductive arrangements have been in use for many years. However, they suffer from a number of disadvantages.

In particular, in both the continuous wave NMR apparatus and the pulse NMR apparatus, the radio frequency excitation signal is applied to the sample inductively by means of a coil, and the nuclear precession signal is read out via inductive coupling. This necessarily introduces constraints, both physical and electronic on the performance of the system. Physically, the coil geometry may be restricted or determined by the nature and size of the sample. Further, an inherent electronic problem associated with the traditional approach is that the transmitter coil couples to the receiving coil inductively, leading to saturation of the receiver amplifier and a subsequent dead time during which the system recovers from overload. Numerous measures have been taken to alleviate this problem, including ensuring that the transmitter and receiver coils are perpendicular to each other, adding diode protection circuits, and the use of quarter wave transmission lines. However, despite these measures the inherent difficulty remains that a large amplitude RF transmitter pulse must be coupled to the sample, and that a small but significant proportion of this will couple inductively to the receiver coil and hence saturate the amplifier system.

SUMMARY OF THE INVENTION

The present invention seeks to overcome the problems described above and to provide a novel means of NMR signal detection.

The invention further seeks to replace the conventional inductive approach to signal detection in NMR apparatus with electric field detection of NMR signals.

The invention also seeks to employ a specially designed electric potential sensor for the electric field detection of an NMR signal from a sample.

According to one aspect of the present invention, there is provided a nuclear magnetic resonance apparatus comprising:

means for applying a static magnetic field to a sample under investigation, a radio frequency circuit arranged to be inductively coupled to the sample by means of an oscillating magnetic field disposed generally perpendicular to the static magnetic field for applying an excitation signal to the sample, and an electric potential sensor for detecting the excitation of the sample and for generating a detection output, wherein the electric potential sensor comprises an electrode placed generally perpendicular to the axis of the oscillating magnetic field for capacitively coupling the electric potential sensor to the sample.

According to another aspect of the present invention, there is provided method of nuclear magnetic resonance signal detection, comprising:

applying a static magnetic field to a sample under investigation, employing an oscillating magnetic field disposed generally perpendicular to the static magnetic field for inductively applying an excitation signal to the sample, and capacitively coupling an electrode to the sample for detecting the excitation of the sample and generating a detection output, the electrode being placed generally perpendicular to the axis of the oscillating magnetic field.

The invention thus replaces the conventional magnetic (inductive) readout system with an electric (capacitive) one.

It is believed that by comparison with the prior art, a number of possible advantages accrue from the invention as described, namely:

- The problem of cross coupling between transmitter and receiver coils in the conventional apparatus is avoided, thereby reducing recovery and dead times in the receiver system.
- A simpler implementation is possible, requiring no front-end tuned trap, quarter wave line or crossed diode networks on the receiver side. A simple gating of a preamplifier is found to be sufficient.
- The use of an untuned (broadband) receiver system allows several nuclear species to be measured simultaneously.
- Smaller probe sizes reduce filling factor problems, which exist in conventional systems, allowing the imaging of very small sample volumes.
- High spatial resolution may be achieved using the intrinsic resolution of electric field probes. This will enable raster scanning, rather than field gradient techniques, to be used for imaging applications.

BRIEF DESCRIPTION OF THE DRAWINGS

The invention will be described further, by way of example, with reference to the accompanying drawings, in which:

FIGS. 16 and 17 are graphs showing a comparison of pulse NMR data obtained respectively using conventional pulse NMR apparatus and the pulse NMR system of FIG. 11, in which FIG. 16 shows a respective free induction decay signal in both cases and FIG. 17 is an identical plot for the situation where there is no static magnetic field and therefore no free induction decay signal in either case.

DETAILED DESCRIPTION OF PREFERRED EMBODIMENTS

Theory of the Use of Electric Potential Sensors

The present invention proposes to employ an electric field sensor in place of the known inductive sensor arrangement of FIG. 2 for signal detection in NMR apparatus.

The principle of operation for electric field detection of NMR signals is to utilise the electric field (E) associated with the precessing magnetic field (B) of the nuclear spins. From the theory of electromagnetism for the far field approximation of a dipole, it is known that:

$$|E|=c|B|$$

where c is the velocity of light. According to the present invention, an electric field sensor is provided for coupling, via a capacitive mechanism, to a sample in order to acquire the NMR signal.

The electric field vector (E) is perpendicular to the magnetic field component (B) and rotating at the Larmor precession frequency. Formally, the two components are related by a Maxwell equation:

$$\mathrm{Curl}\, E = -\delta B/\delta t$$

This provides the information needed to position an electrode arrangement for the sensor in order to pick up the electric field component. As described below, the electrode arrangement is placed perpendicular to the axis of the coil providing the RF input. The electrode arrangement may comprise a single electrode arranged to measure the potential with respect to the signal ground, or it may comprise a pair of electrodes. In the following description, it will be assumed that each sensor only includes a single electrode. It is advantageous to use two electrometers or sensors in a differential arrangement to enhance the signal to noise ratio by noise subtraction. For this to operate effectively, the to electrodes of the two sensors must be at two unequal radial distances from the centre of the coil axis in order to provide a differential signal for amplification.

NMR Apparatus Employing an Electric Potential Sensor

Figure 6:
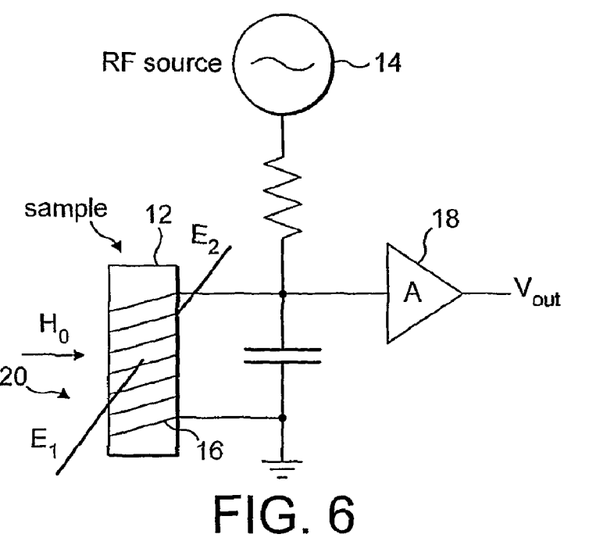
FIG. 6 is a circuit diagram of NMR apparatus according to the present invention.

FIG. 6 illustrates the implementation of this principle in an electric field sensor arrangement 20, which is applicable to both continuous wave and pulse NMR applications. The apparatus of FIG. 6 is similar to that of FIG. 2, except in that two electric field sensors $E_1$ and $E_2$ have been added. Similar reference numerals designate the same elements and therefore need not be further described. The amplifier 18 is not essential but is retained to allow a magnetic signal to be acquired at the same time as the electric signal, for comparison purposes.

Figure 7:
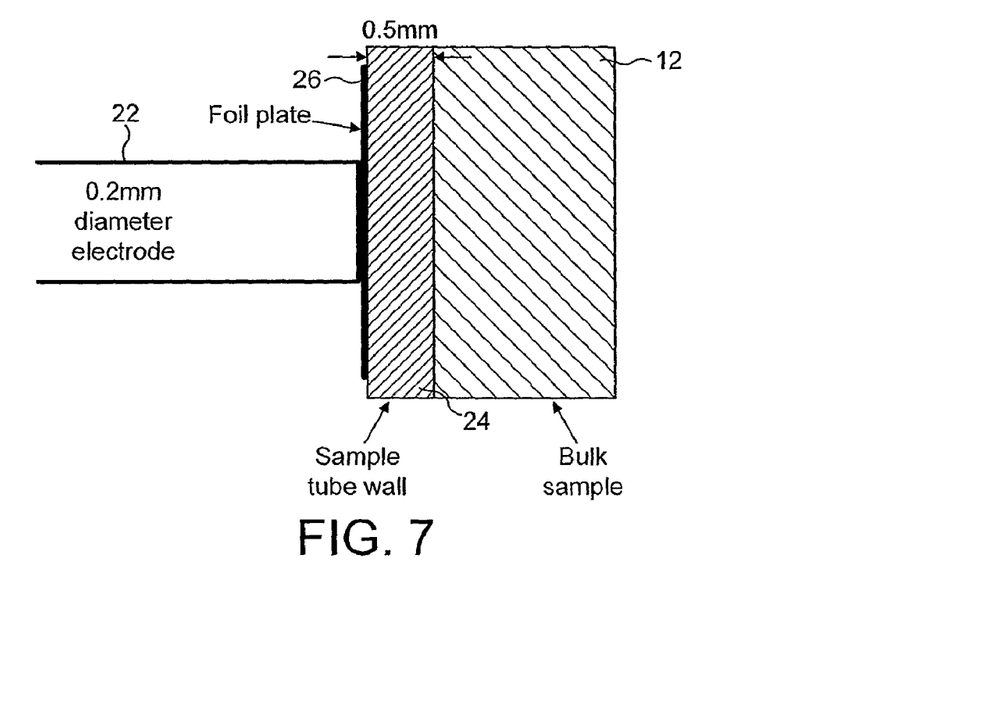
FIG. 7 is a diagram of an electrode of the apparatus of FIG. 6.

In order to acquire the electric field NMR signal, each such sensor E is coupled to the sample 12 through a glass sample tube 24 via a capacitive mechanism by means of a respective electrode 22, such as the one shown in FIG. 7. For most applications, the capacitive coupling will be very weak. For example, the coupling capacitance between the tip of a 0.2 mm diameter electrode 22 and the sample 12 through a 0.5 mm thick glass sample tube 24 is estimated to be of the order of a few $\times 10^{-14}$ F. This may be increased to ~0.5 pF by the addition of a small (~1 $mm^2$) foil electrode plate 26 on the tip of the sensor electrode 22 as shown.

In order to acquire the NMR signal without significant attenuation, it is necessary for each sensor E to have an input capacitance comparable to or lower than this coupling capacitance. It is also a requirement that the sensor has sufficient bandwidth and slew rate to allow efficient amplification of the RF NMR signal. In the present example, the operating frequency was chosen to be between 1.5 MHz and 2 MHz. Typically, NMR systems operate over the whole of the RF spectrum up to many hundreds of MHz.

It should be noted that the intrinsic spatial resolution of each electric field sensor E is limited by the physical size of the tip of the electrode 22. This is scalable over a wide range and has been shown to operate from <1 µm to ~10 cm. In principle, the resolution can range from the atomic scale (~nm) to many metres depending on the application. The spatial resolution can easily be improved if a sample tube 24 with a thinner wall is used, or if the electrode 22 is insulated by a thin dielectric layer, so as to maintain the coupling capacitance with a much smaller cross sectional area.

Thus, the design of each electric field sensor E for this application must meet certain stringent requirements such as: low input capacitance, and high operating bandwidth.

Figure 8:
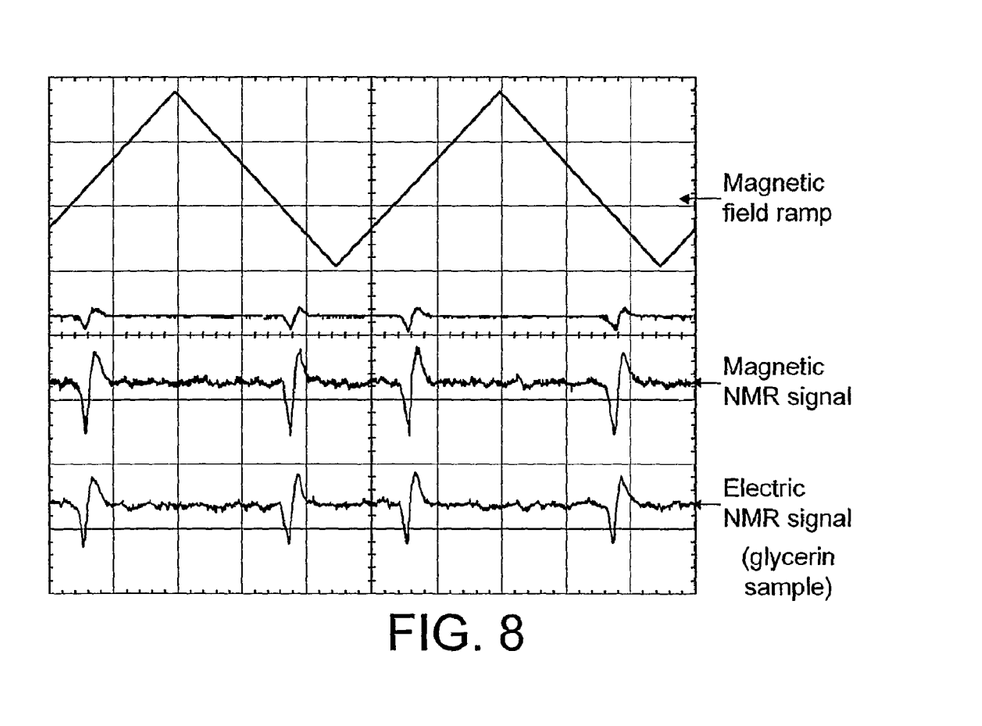
FIG. 8 is a signal diagram comparing an output signal of the apparatus of FIG. 6 with the output signal of the apparatus of FIG. 2 when set up for continuous wave operation.

FIG. 8 shows comparison data obtained from the NMR apparatus of FIG. 6, when operated as continuous wave NMR apparatus, including particularly the output signal from the amplifier 18 representing the conventional magnetic NMR signal and that obtained from the sensors E representing the new electric field NMR signal. It is evident that the outputs are comparable in each case.

A Specific Design of Electric Field Sensor

Figure 9:
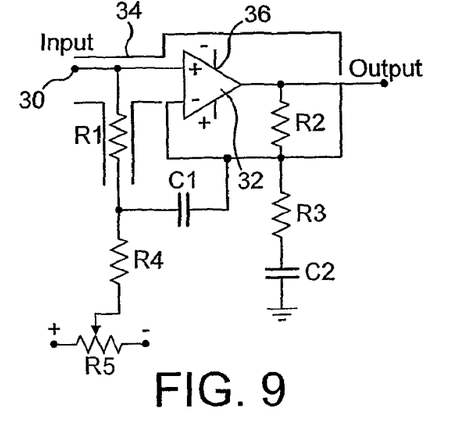
FIG. 9 is a circuit diagram of an electric potential sensor of FIG. 6.

FIG. 9 shows a schematic circuit diagram for a respective one of the sensors E of FIG. 6.

As shown, an input 30 includes the electrode 22 and supplies the signal from this electrode to an operational amplifier 32. The input impedance of the amplifier 32 is enhanced by the use of guarding, which is a positive feedback technique and which involves physically surrounding all the high impedance parts of the circuit, including the input circuitry, wiring and electrode 22, as completely as possible with a guard 34 driven by the output of the amplifier 32. The surfaces of the guard 34 enclose and are maintained at the same potential as the input 30. Charging effects on stray capacitance are alleviated by maintaining the same potential (signal potential) on the guard 34 as on the input electrode 22.

The amplifier 32 is configured as a non-inverting amplifier with a voltage gain determined by a series connection of two resistors, R2 and R3, having typical values of 1-100 kΩ. A capacitor C2 (typically ~1 µF) in series with the resistors R2 and R3 acts as a high pass filter by reducing the gain to unity at zero frequency (DC). This reduces the low frequency noise pick up considerably and thus aids the signal to noise ratio and stability of the sensor E.

Another positive feedback technique in the form of bootstrapping is also employed in order to increase the effective input impedance of the amplifier 32 at signal frequency. More especially, a resistor R1 (typically in the range 1MΩ to 100 GΩ) connected to the input 30 provides a DC input bias current, via resistors R4 and R5 (typically 1-100 kΩ), that is required by the amplifier 32 for stable operation. A capacitor C1 is utilised to apply the output voltage of the amplifier 32 to the junction of the resistors R1, R4 so that the input voltage appears at both terminals of the upper resistor R1, resulting in zero current flow and an infinite impedance. Thus, the resistor R1 is bootstrapped by a positive feedback signal provided by the capacitor C1 (typically 10 nF to 100 µF). This ensures that the potential across the resistor R1 at the signal frequency is kept as small as possible, thus effectively increasing or bootstrapping the value of the resistor R1 many times. Adjustment of the resistor R5 permits the DC operating point of the amplifier 32 to be zeroed. The capacitor C1 together with the resistors R4 and R5 also act as a high pass filter by restricting the range of frequencies over which the bootstrapping will operate effectively.

The sensor E may also have the facility for gating the amplifier 32 rapidly, which in application of the sensor in pulse NMR apparatus enables the apparatus 20 to be protected from the large amplitude RF pulses that are applied to the sample 12 and thus allows the complex protection circuitry conventionally associated with the receiver side of an NMR spectrometer to be dispensed with. Gating of the amplifier 32 is achieved using an appropriate voltage signal applied to the enable pin 36 of the amplifier 32. The symbols + and − in FIG. 9 refer to the power supply connections for the amplifier 32.

For the purposes of evaluation, a test electric field sensor for use in the NMR apparatus shown in FIG. 6 was produced according to the design of FIG. 9 and based on a commercial operational amplifier with the following specifications:

| | |
| --- | --- |
| Gain Bandwidth Product | 200 MHz |
| Slew Rate | 200 V/µs |
| Input Capacitance | 0.5 pF |
| Gating facility | 25 ns off, 200 ns on |
| Voltage Noise | 10 nV/$\sqrt{Hz}$ |

Using the illustrated circuit, the operational bandwidth is typically 5 kHz to 10 MHz with an open circuit voltage noise of 30-70 nV/$\sqrt{Hz}$.

A particular benefit of the design of sensor E used here is the ability to gate the amplifier 32. This allows the receiver chain to be isolated during the transmitter pulse without the need for either diode networks or quarter wave lines, as would usually be the case. In principle, the off and on times for this procedure are 25 ns and 200 ns respectively, extremely fast by the standards of NMR recovery time in conventional systems.

Continuous Wave NMR System According to the Invention

Figure 10:
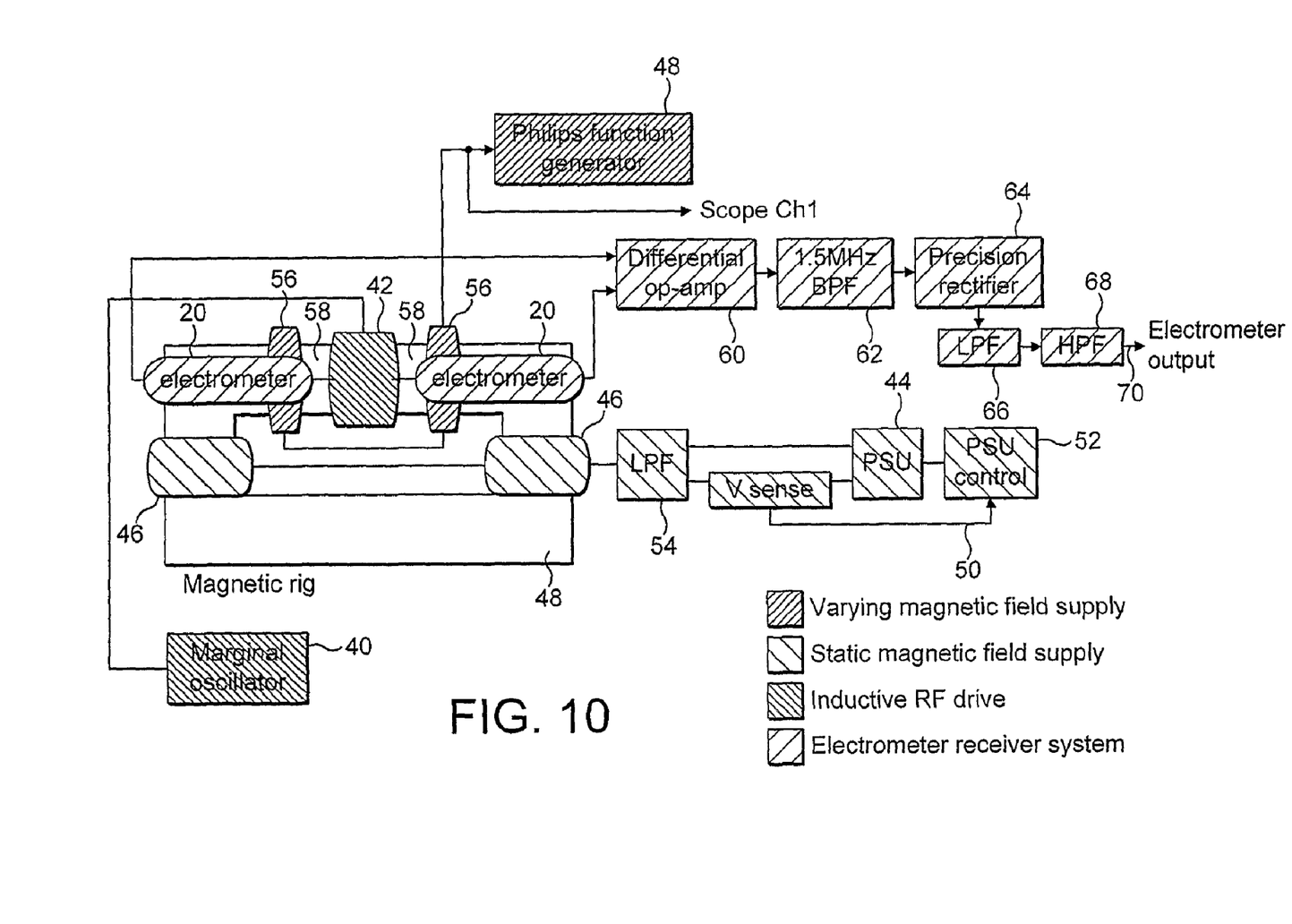
FIG. 10 is a block diagram of a continuous wave NMR system according to the invention.

FIG. 10 shows a block diagram for a continuous wave NMR system according to the invention, where the continuous wave excitation signal is provided by a conventional marginal oscillator and the static magnetic field $H_o$ is created by a simple electromagnet. More particularly, the functions of RF source and signal amplifier are combined into a marginal oscillator 40 connected to a resonant circuit 42 surrounding the sample 12. The static magnetic field section of the system includes a feedback stabilised power supply (PSU) 44 designed to maintain a constant current, and hence a constant magnetic field, through the coils 46 of an electromagnet 48. For this purpose, the feedback loop 50 for the PSU 44 includes a PSU control circuit 52, and the output of the PSU 44 is supplied by way of a low pass filter 54 to the coils 46. Added to this static field, is a slowly time varying field created by a function generator 48 and fed to a secondary pair of coils 56 fitted to the pole pieces 58 of the electromagnet 48. Two electric field detection sensors 20 as already described and as shown in FIGS. 6 and 9 are connected to a differential operational amplifier 60, and the output of the operational amplifier 60 is supplied to a band pass filter 62 and thence to a precision rectifier 64 and via a low pass filter 66 and a high pass filter 68 to an output 70.

Pulse NMR System According to the Invention

Figure 11:
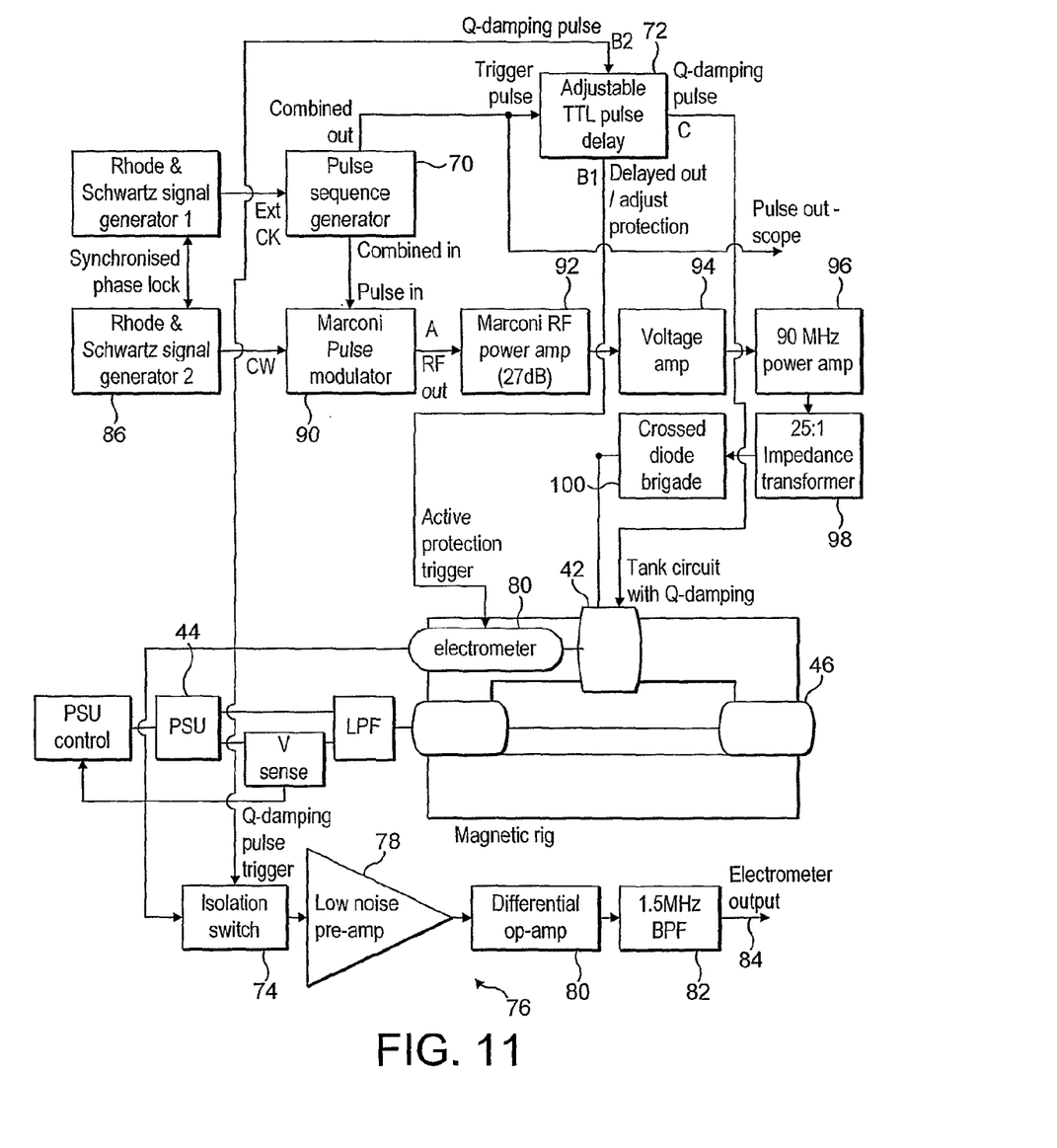
FIG. 11 is a block diagram of a pulse NMR system according to the invention.

Another NMR system according to the invention is shown in FIG. 11 comprising a pulse NMR system. This pulse NMR system includes some of the same parts as the continuous wave NMR system illustrated in FIG. 10, and the same parts are designated by the same reference numerals and need not be described further. In particular, the pulse NMR system of FIG. 11 includes a static field power supply section that is identical to that used for the continuous wave system. However, to implement a pulse system, the RF electronics must be modified to include a high power (~10 W) coherent source, a pulse modulator, appropriate diode isolation circuits and an active Q damping mechanism for the resonant transmitter probe. In addition, it is necessary to optimise parameters such as the pulse amplitude and duration as well as the mark to space ratio of the pulse sequence.

In the present embodiment, a single electric field sensor 20 as described with reference to and as shown in FIGS. 6 and 9 is provided, the NMR signal being coupled to the electric field sensor 20 via capacitive coupling. The sensor 20 is electronically gated by means of gating pulses supplied by a pulse sequence generator 70 through an adjustable transistor-transistor logic (TTL) pulse delay circuit 72, which also supplies blanking pulses for controlling a sensor isolation switch or circuit 74 as well as Q damping pulses for controlling a Q damping circuit within the resonant circuit 42 as described below. It is to be noted that a conventional magnetic signal receiver (inductively coupled system) would require elaborate measures in order to prevent the large RF pulse from destroying or at least saturating the receiver electronics. By comparison, the electric field sensor requires no such protection, since the electronic gating is sufficient and much simpler to implement.

The output of the sensor 20 is connected to the isolation circuit 74 situated between the output of the sensor 20 and the input to subsequent amplification stages 76. This isolation circuit 74 is controlled by the blanking pulses supplied by the TTL pulse delay circuit 72 and serves to isolate the output side of the system during and immediately following the application of the RF pulses to the resonant circuit 42. Such isolation aids the recovery of the later stage amplifiers after the RF pulse has ended. In this instance, two further stages of amplification are used, including a signal preamplifier 78 and an amplifier 80, followed by a bandpass filter 82 designed to reject unwanted noise. The output of the bandpass filter 82 constitutes the output 84 of the system.

Figure 12:
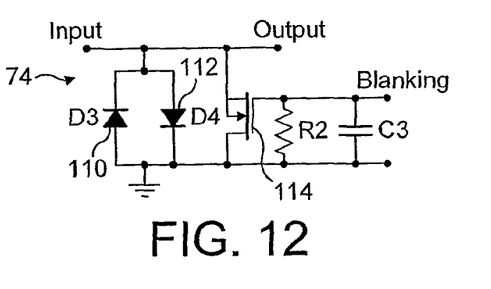
FIGS. 12 to 14 are circuit diagrams of certain of the blocks shown in FIG. 11.

FIG. 12 shows the isolation circuit 74 from FIG. 11, which is used after the electric potential sensor 20 to protect the following amplifiers 80, 82 from overload and saturation and aid their recovery. As shown, the circuit 74 comprises a parallel combination of crossed diodes 110, 112 and an FET 114 presenting a low impedance termination to large pulses (since the diodes will conduct under these conditions and the FET 114 will be turned on by the blanking signal during the RF pulse). This, and gating the electric potential sensor 20, are the main protective measures necessary in order to acquire an electric field NMR signal and are significantly less complex than would be required for the conventional magnetic signal approach. Note also that no additional circuitry is required before the electric field sensor 20, whereas conventional NMR systems need circuits to protect the preamplifier stage from overload and to aid signal recovery.

The RF pulse in the system of FIG. 11 is generated using two phase locked RF synthesisers 86, 88. One such synthesiser 86 acts as a generator providing the RF pulse, while the other such synthesiser 88 provides a reference frequency for the pulse generator 86. The continuous RF output from the first synthesiser 86 is fed to a pulse modulator 90, which is controlled using a TTL pulse produced by the pulse sequence generator 70. The resulting RF pulse is then amplified to produce the requisite power. This is achieved using a commercial power amplifier 92, a voltage amplifier 94 based on an operational amplifier, and a second power amplifier 96 with a 50Ω matching transformer 98. The RF pulse is then passed through a diode network 100 to the resonant circuit 42. This network 100 is arranged to isolate the resonant circuit 42 from the power amplifier chain when the pulse is off.

Figure 13:
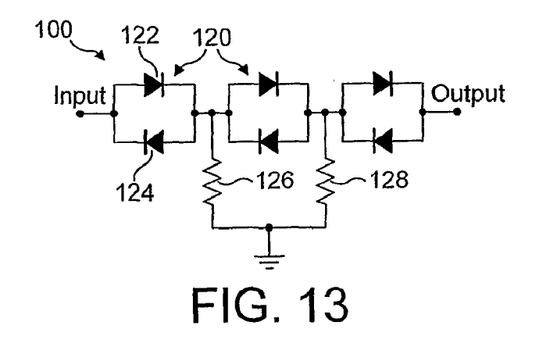

The RF pulse diode isolation network 100 is further illustrated in FIG. 13 and comprises a crossed diode brigade designed to prevent noise from the RF power amplifier 96 coupling to the resonant circuit 42 during the period when the pulse is off and the NMR signal is being acquired. As shown, the network 100 comprises pairs 120 of crossed diodes 122, 124 presenting low impedance to large signals (larger than the forward turn on voltage of ~0.6V) and a relatively high impedance to small signals (e.g. the amplifier noise). This high impedance forms an effective potential divider with a parallel connection of a pair of resistors 126, 128 typically having a resistance of ~470Ω each. Each pair of diodes 122, 124 provides additional attenuation such that the cascaded total effect is of the order of −60 dB.

As already mentioned, the pulse sequence generator 70 and the associated TTL pulse delay unit 72 generate a series of gating pulses for gating the sensor 20 and a series of blanking pulses for controlling the isolation circuit 74. They also generate a series of Q damping pulses, which are used to control the Q damping circuit within the resonant circuit 42. Q damping is the process of dumping, as rapidly as possible, the energy stored in the resonant circuit 42 at the end of each RF pulse. Thus, each Q damping pulse is arranged to commence at the end of an RF pulse and to continue for a period of time optimised as the shortest possible time consistent with the energy stored in the resonant circuit being dumped. This enables the very small free induction decay signal to be seen more easily and is achieved using an FET switch to terminate excitation by the resonant circuit with a resistor which meets the criterion for critical damping.

Figure 14:
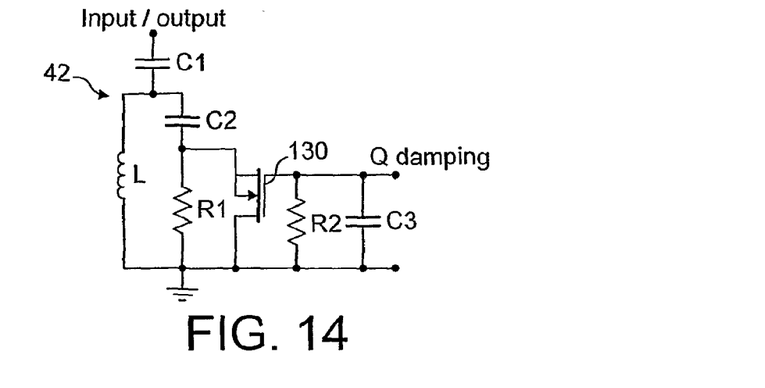

FIG. 14 further illustrates the resonant circuit 42 used to probe the sample 12 and including the active Q damping circuit. The resonant frequency of the circuit is determined by a parallel connection of an inductance L and a capacitance C2. For this example, typical values for L and C2 would be in the region respectively of 10 μH and 470 pF. A capacitor C1 providing an input/output to the resonant circuit 42 is chosen to provide an optimum impedance match between the resonant circuit 42 and the transmission line cables (50Ω) used to couple to the RF power amplifier 92 and the signal preamplifier 78. Typically, C1 may be around 39 pF. An FET 130 is normally in the on state, but is switched off during the Q damping process. This action results in a resistor R1 connected across the FET 130 being switched into a series connection with the resonant circuit 42. The value for R1 is chosen to satisfy the critical damping condition ($R^2=4$ L/C) and may typically be ~250Ω, which results in the rapid dissipation of the energy stored in the resonant circuit 42 at the end of the RF pulse.

Figure 15:
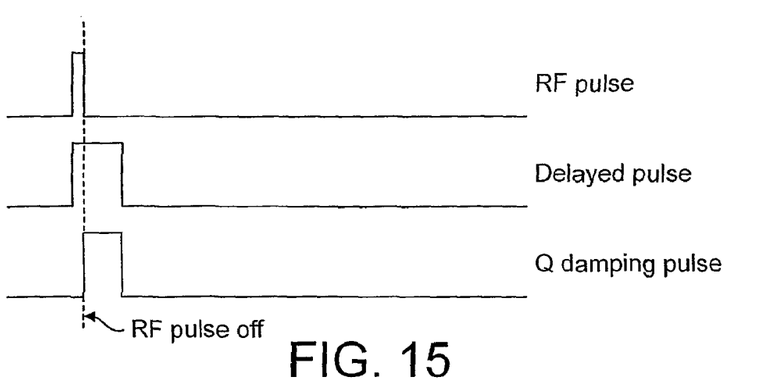
FIG. 15 is a signal diagram representing the signals at various points of the system of FIG. 11.

The RF pulse typically consists of a short (e.g. 20 μs) pulse followed by a long (1 ms to 10 s) gap, during which the sensor signal is acquired. The pulse synthesiser/generator 86 provides this short pulse as an output at point A of the system in FIG. 11, and the phase locked synthesiser 88 in conjunction with the pulse delay circuit 72 produces a delayed pulse as an output at points B1 and B2 of the system. The pulse at point B1 comprises the gating pulse for controlling the sensor 20, while the pulse at point B2 is used to control the FET isolation switch 114 in the isolation circuit 74. The Q damping pulse is generated as another output of the pulse delay circuit 72 at point C of the system and effectively consists of the overlap between the short pulse and the delayed blanking pulse. The Q damping pulse therefore exists for the time interval between the end of the RF pulse and the end of the blanking pulse. The duration of the Q damping pulse is optimised to give the shortest recovery time for the resonant circuit after the end of the RF pulse. The timing diagram in FIG. 15 illustrates the relationship of these pulses and demonstrates that the delayed pulse and the Q damping pulse terminate together, at which point the sensor 20 will have been gated, the output amplifiers 78, 80 will have been isolated from the RF pulse and the energy stored in the resonant circuit 42 will have dissipated and the system is ready to acquire the free induction decay signal.

The bandwidth limiting filter 82 is included in order to reject unwanted noise and so improve the signal to noise ratio. Signal averaging of the data is also used to improve the signal to noise ratio. This is only made possible because the pulse sequence generator 86 is phase locked to the second RF frequency synthesiser 88. This means that the phase of the RF contained in each pulse is the same so that the data will build up to provide a true result rather than time average to zero.

Figure 16:
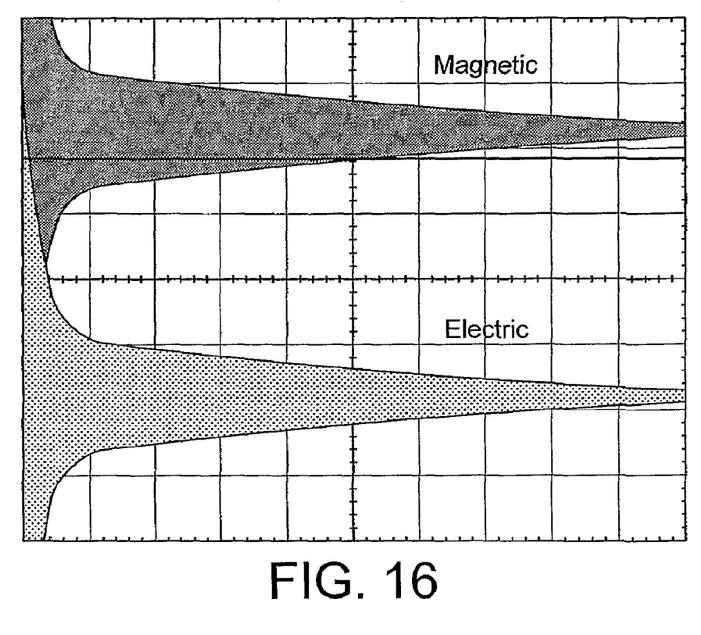
Figure 17:
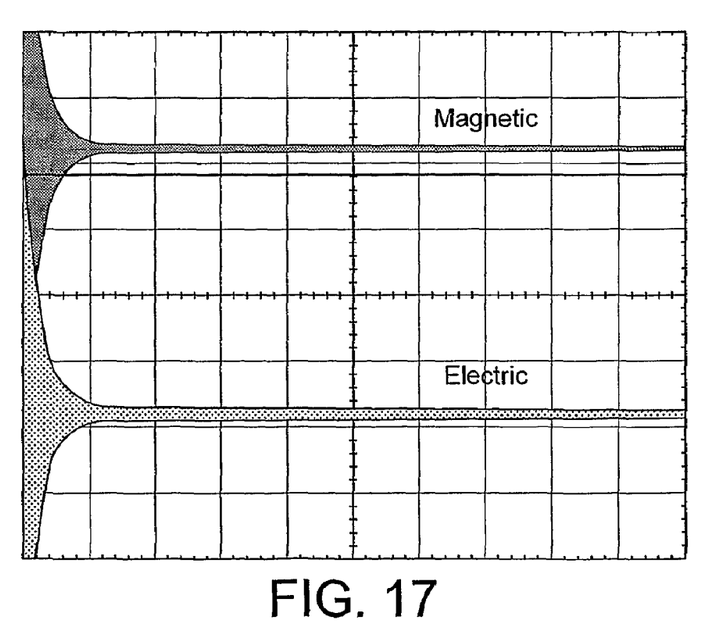

It should be noted that the described electric field sensor arrangement according to the invention offers a significantly simpler option for acquiring an NMR signal than does the conventional magnetic arrangement. FIGS. 16 and 17 show comparable results for both arrangements using a similar circuit arrangement for generating the RF pulses, and a similar arrangement for the electromagnet 48 but the different sensor approaches. The plot in each case is the result of ~100 averages. In FIG. 16 comparative electric and magnetic signals are shown in the presence of the static magnetic bias field and for a glycerine sample as before, and in FIG. 17 they are shown in the absence of a static magnetic bias field. Clearly in the latter case, only the recovery of the resonant circuit at the start of the trace is seen and no NMR decay signal (FID signal) thereafter.

Figure 18:
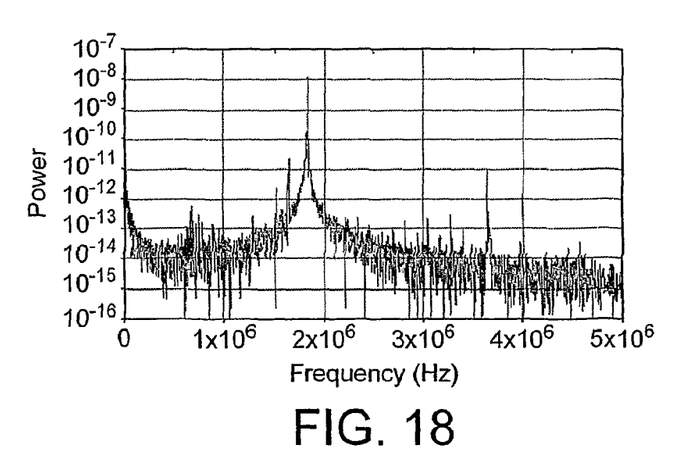
FIG. 18 is a graph representing a Fourier transform of the data obtained from the apparatus of FIG. 11 as shown in FIG. 16.

Since information is contained in the frequency of the precession, it is usual to present the data in the frequency domain, for example by means of a Fourier transform (FFT) to obtain the NMR spectrum of the sample. The result of Fourier transforming the electric field data of FIG. 16 is shown in FIG. 18. One clear resonance peak corresponding to the NMR signal is displayed at 1.825 MHz for the glycerine sample, as expected. All other peaks are at least a factor of 1000 smaller and are the result of either noise or non-linear behaviour in the system.

An estimate of the amplitude of the output electric field signal may be made as follows. First, in a conventional magnetic system as mentioned above, the output voltage (V) from the magnetic channel may be used to estimate the magnetic field (B) in the resonant probe coil due to the observed free induction decay signal using the equation:

$$B = \frac{\dot{\Phi}}{QAf}$$

where $$V = -\dot{\Phi}, \dot{\Phi} = \frac{d\Phi}{dt},$$

Φ is the magnetic flux in the coil, Q is the quality factor of the resonant probe circuit, A is the cross sectional area of the coil and f is the precession frequency $$\left( = \frac{\omega_0}{2\pi} \right).$$

For typical data acquired using such a conventional system, this corresponds to $B=1.8\times10^{-10}$ T. Next, such results may be converted to an electric field (E) using the plane wave approximation:

$$|\underline{E}|=c|\underline{B}|$$

where c is the velocity of light. This gives an electric field of 54 mV/m. The final step is to calculate the voltage at the electric sensors of the invention due to this electric field using the equation:

$$V_{out}=|E|d$$

where d is the spacing of the electric sensors. For the example used here, this results in an estimated voltage at the input of the sensors of 6 μV. This corresponds to an estimated output voltage of ~180 mV for the electric field channel, which is in good agreement with the observed output of ~150 mV.

Various modifications are possible to the described embodiments within the scope of the invention.

For example, the embodiment of FIG. 6 is described as having two electric field sensors, whereas that of FIG. 11 is described as having one. In practice, any number of the sensors may be provided from one upwards. The use of two such sensors, however, employed differentially has the advantage of improving the signal to noise ratio by comparison with an arrangement employing only one such sensor.

Further, the resistor R1 included in the FIG. 9 circuit for providing a DC input bias may be replaced with a number of other components serving the same purpose, such as for example a diode or a field effect transistor.

The present invention as described is applicable both to continuous wave NMR apparatus and to pulse NMR apparatus, and offers a number of significant advantages by comparison with the conventional inductive approach to NMR signal detection.

In particular, the problem of cross coupling between transmitter and receiver coils in the conventional apparatus is avoided, thereby reducing recovery and dead times in the receiver system. Furthermore, the implementation of an electric field sensor is greatly simplified by comparison with a conventional inductive sensor and requires no front-end tuned trap, quarter wave line or crossed diode networks on the receiver side. A simple gating of the preamplifier is found to be sufficient for protecting the sensor.

It is also possible to employ smaller probe sizes than in the conventional systems and the sensor is only strongly coupled to a relatively small part of the sample. It is anticipated that this will reduce filling factor problems, which exist in conventional systems when using very small sample volumes. The present invention, therefore, should facilitate the imaging of very small sample volumes.

In addition, high spatial resolution may be achieved using the intrinsic resolution of electric field probes.

Further, the sensor electrodes are untuned and therefore intrinsically broadband. The use of an untuned (broadband) receiver system may allow several nuclear species to be measured simultaneously.

The invention claimed is:

1. Nuclear magnetic resonance apparatus comprising:
   means for applying a static magnetic field to a sample under investigation,
   a radio frequency circuit arranged to be inductively coupled to the sample by means of an oscillating magnetic field disposed generally perpendicular to the static magnetic field for applying an excitation signal to the sample for generating a nuclear spin precessing magnetic field, and
   an electric potential sensor employed for signal detection by detecting excitation of the sample responsive to the excitation signal and generating a detection output based on an electric field associated with the precessing magnetic field,
   wherein the electric potential sensor comprises an electrode placed generally perpendicular to the axis of the oscillating magnetic field for capacitively coupling the electric potential sensor to the sample.

2. Apparatus according to claim 1, comprising two said electric potential sensors, in which the electrodes of the two sensors are placed generally perpendicular to the said axis and are disposed at different radial distances from the said axis.

3. Apparatus according to claim 1, in which the electric potential sensor comprises an operational amplifier having an input connected to the electrode and arranged to provide a detection output, and a positive feedback arrangement for enhancing the input impedance of the operational amplifier.

4. Apparatus according to claim 3, in which the positive feedback arrangement includes a guard surrounding respective high impedance parts of the sensor circuitry, the guard being driven by the output of the operational amplifier.

5. Apparatus according to claim 4, in which the guard surrounds the electrode and an input to the operational amplifier.

6. Apparatus according to claim 3, in which the positive feedback arrangement includes a bootstrapping circuit.

7. Apparatus according to claim 6, in which the bootstrapping circuit comprises an input bias element for providing a DC input bias current to the operational amplifier, and a capacitor for applying the output voltage of the operational amplifier to the input bias element to ensure that the potential across the resistor is minimised.

8. Apparatus according to claim 3, in which the electric potential sensor comprises a high pass filter for reducing the gain of the operational amplifier to unity at zero frequency.

9. Apparatus according to claim 3, in which the electric potential sensor further comprises a gating arrangement for the operational amplifier.

10. Apparatus according to claim 1, in which the electrode comprises an electrode pin having a foil electrode plate mounted at its tip.

11. Apparatus according to claim 1, in which the electrode is insulated by a thin dielectric layer.

12. Apparatus according to claim 1, comprising an electromagnet as a static magnetic field generator.

13. Apparatus according to claim 1, employed as continuous wave nuclear magnetic resonance apparatus.

14. Apparatus according to claim 13, comprising a function generator for providing a time variation of the static magnetic field, and in which the radio frequency circuit comprises a marginal oscillator providing a radio frequency source.

15. Apparatus according to claim 13, comprising two of the electric potential sensors connected to a differential operational amplifier for providing a detection output.

16. Apparatus according to claim 1, employed as pulse nuclear magnetic resonance apparatus.

17. Apparatus according to claim 16, in which the radio frequency circuit comprises a radio frequency generator including phase locked radio frequency synthesisers, and a pulse modulator.

18. Apparatus according to claim 16, in which the radio frequency circuit comprises a radio frequency generator for generating a radio frequency pulse sequence, a resonant circuit for providing the inductive coupling to the sample, and a pulse isolation network for isolating the radio frequency generator from the resonant circuit between the radio frequency pulses in the pulse sequence.

19. Apparatus according to claim 16, in which the radio frequency circuit comprises a radio frequency generator for generating a radio frequency pulse sequence, a resonant circuit for providing the inductive coupling to the sample, and a Q damping circuit for dissipating energy stored in the resonant circuit at the end of each pulse in the pulse sequence.

20. Apparatus according to claim 19, further comprising means for generating blanking pulses to control the Q damping circuit.

21. Apparatus according to claim 16, further comprising a sensor isolation circuit arranged at the output of the electric potential sensor for protecting subsequent signal processing stages.

22. Apparatus according to claim 20, further comprising means for generating blanking pulses to control the sensor isolation circuit.

23. A method of nuclear magnetic resonance signal detection, comprising:
    applying a static magnetic field to a sample under investigation,
    employing an oscillating magnetic field disposed generally perpendicular to the static magnetic field for inductively applying an excitation signal to the sample for generating a nuclear spin precessing magnetic field, and
    employing an electric potential sensor for signal detection by detecting excitation of the sample responsive to the excitation signal and generating a detection output based on an electric field associated with the precessing magnetic field, wherein said step of detecting comprises placing an electrode of the electric potential sensor generally perpendicular to the axis of the oscillating magnetic field and capacitively coupling the electrode to the sample.

24. A method according to claim 23, comprising employing two said electric potential sensors, and placing the electrodes of the two sensors generally perpendicular to the said axis and at different radial distances from the said axis.

25. A method according to claim 23, comprising employing an operational amplifier connected to the electrode for generating the detection output, and utilising positive feedback for enhancing the input impedance of the operational amplifier.

26. A method according to claim 25, comprising guarding respective high impedance parts of the operational amplifier circuitry.

27. A method according to claim 25, comprising bootstrapping an input bias element providing a DC input bias current to the operational amplifier.

28. A method according to claim 25, comprising reducing the gain of the operational amplifier to unity at zero frequency.

29. A method according to claim 25, comprising gating the operational amplifier.

30. A method according to claim 25, comprising generating a time variation of one of the static magnetic field and the oscillating magnetic field.

31. A method according to claim 23, comprising generating a radio frequency pulse sequence for producing the oscillating magnetic field.

32. A method according to claim 31, comprising isolating the means for generating the radio frequency pulse sequence between the radio frequency pulses in the pulse sequence.

33. A method according to claim 31, comprising dissipating energy stored in a resonant circuit for inductively coupling the oscillating magnetic field to the sample at the end of each pulse in the pulse sequence.

34. A method according to claim 33, further comprising generating blanking pulses to control the timing of the dissipation of energy.

35. A method according to claim 23, further comprising isolating a resonant circuit for inductively coupling the oscillating magnetic field to the sample from the detection output following the end of each pulse in the pulse sequence.

36. A method according to claim 35, further comprising generating blanking pulses to control the timing of the isolation.

* * * * *